US011224910B2

(12) United States Patent
Young et al.

(10) Patent No.: US 11,224,910 B2
(45) Date of Patent: Jan. 18, 2022

(54) METHOD OF FORMING A BEND OF A PREDETERMINED BEND ANGLE IN A SHAPE MEMORY ALLOY WIRE AND METHOD OF MAKING A SELF-EXPANDING STENT

(71) Applicant: Cook Medical Technologies LLC, Bloomington, IN (US)

(72) Inventors: Ronan T. Young, Spencer, IN (US); Erik A. Rasmussen, Slagelse (DK); Jens Schultz, Skovlunde (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 378 days.

(21) Appl. No.: 15/909,081

(22) Filed: Mar. 1, 2018

(65) Prior Publication Data

US 2018/0250732 A1   Sep. 6, 2018

Related U.S. Application Data

(60) Provisional application No. 62/466,610, filed on Mar. 3, 2017.

(51) Int. Cl.
*B21F 45/00* (2006.01)
*A61F 2/88* (2006.01)
(Continued)

(52) U.S. Cl.
CPC .............. *B21F 45/008* (2013.01); *A61F 2/07* (2013.01); *A61F 2/88* (2013.01); *A61F 2/92* (2013.01);
(Continued)

(58) Field of Classification Search
CPC .......... B21F 1/00; B21F 1/004; B21F 45/008; B21F 45/00; A61F 2/86; A61F 2/88;
(Continued)

(56) References Cited

U.S. PATENT DOCUMENTS 4,631,094 A * 12/1986 Simpson ................. C22F 1/006
148/402
4,665,906 A * 5/1987 Jervis ....................... A61C 7/12
606/78
(Continued)

FOREIGN PATENT DOCUMENTS

WO   WO 95/32757        12/1995
WO   WO 2013/158218 A1  10/2013

OTHER PUBLICATIONS

"Texture and Strain Measurements from Bending of NiTi", Carl et al. Jul. 2016.*
(Continued)

*Primary Examiner* — Edward T Tolan
(74) *Attorney, Agent, or Firm* — Crowell & Morning LLP

(57) ABSTRACT

A method of making a self-expanding stent entails applying a bend stress sufficient to over-bend a portion of a wire by an amount in a range from about 85% to about 105%, where the wire comprises a Ni—Ti alloy and includes from about 40% to about 46% cold work. The bend stress is then released, thereby forming a bend having a predetermined bend angle in the wire. The application and release of the bend stress are repeated on successive portions of the wire in order to create a series of bends along a length of the wire in a predetermined bend pattern. The wire comprising the predetermined bend pattern is then positioned about a mandrel in an expanded stent geometry and heat set. Thus, a self-expanding stent is formed.

14 Claims, 2 Drawing Sheets

(51) Int. Cl.
  *B21F 1/00* (2006.01)
  *A61F 2/07* (2013.01)
  *A61F 2/92* (2013.01)
  *A61F 2/844* (2013.01)
  *A61F 2/91* (2013.01)

(52) U.S. Cl.
  CPC ............... *B21F 1/00* (2013.01); *B21F 45/00* (2013.01); *A61F 2/844* (2013.01); *A61F 2/91* (2013.01); *A61F 2210/0014* (2013.01); *A61F 2240/001* (2013.01)

(58) Field of Classification Search
  CPC ........ A61F 2210/0014; A61F 2240/001; A61F 2210/0019; A61M 2025/09108; C22F 1/006
  See application file for complete search history.

(56) References Cited

U.S. PATENT DOCUMENTS

| | | | | |
|---|---|---|---|---|
| 4,894,100 | A * | 1/1990 | Yamauchi | C22C 19/03 148/402 |
| 5,080,584 | A * | 1/1992 | Karabin | A61C 7/20 433/20 |
| 5,238,004 | A * | 8/1993 | Sahatjian | A61M 25/09 600/434 |
| 6,022,370 | A | 2/2000 | Tower | |
| 6,068,623 | A * | 5/2000 | Zadno-Azizi | A61M 25/09 600/585 |
| 6,254,550 | B1 | 7/2001 | McNamara | A61M 25/09 600/585 |
| 6,425,887 | B1 * | 7/2002 | McGuckin | A61B 17/3468 604/272 |
| 6,451,025 | B1 * | 9/2002 | Jervis | A61F 2/88 606/108 |
| 6,689,162 | B1 * | 2/2004 | Thompson | A61F 2/06 623/1.18 |
| 7,112,055 | B1 * | 9/2006 | Anukhin | A61F 2/91 249/100 |
| 7,163,550 | B2 * | 1/2007 | Boismier | A61F 2/013 606/200 |
| 8,118,858 | B2 | 2/2012 | Tseng et al. | |
| 8,690,884 | B2 * | 4/2014 | Linderman | A61B 17/8819 606/94 |
| 8,758,268 | B2 * | 6/2014 | Bown | A61M 25/09 148/563 |
| 9,296,034 | B2 | 3/2016 | Costa et al. | |
| 2007/0072147 | A1 * | 3/2007 | Berendt | C22C 19/03 433/102 |
| 2008/0053577 | A1 | 3/2008 | Syed et al. | |
| 2010/0075168 | A1 * | 3/2010 | Schaffer | C22C 19/055 428/544 |
| 2010/0198333 | A1 | 8/2010 | Macatangay et al. | |
| 2010/0269950 | A1 | 10/2010 | Hoff et al. | |
| 2011/0070358 | A1 | 3/2011 | Mauch et al. | |
| 2013/0190772 | A1 * | 7/2013 | Doerr | A61B 17/86 606/104 |
| 2014/0031917 | A1 | 1/2014 | Thompson | |
| 2018/0147616 | A1 * | 5/2018 | Chen | B21D 26/033 |

OTHER PUBLICATIONS

Extended European Search Report in related EP Application No. 18275033.1, dated Jul. 23, 2018 (8 pages).

Civjan, Simon et al., "Potential Applications of Certain Nickel-Titanium (Nitinol) Alloys," *Journal of Dental Research*, 54, 1 (1975) pp. 89-96.

* cited by examiner

METHOD OF FORMING A BEND OF A PREDETERMINED BEND ANGLE IN A SHAPE MEMORY ALLOY WIRE AND METHOD OF MAKING A SELF-EXPANDING STENT

RELATED APPLICATION

The present patent document claims the benefit of 35 U.S.C. § 119(e) to U.S. Provisional Patent Application No. 62/466,610, which was filed on Mar. 3, 2017, and is hereby incorporated by reference in its entirety.

TECHNICAL FIELD

The present disclosure is related generally to medical devices and more particularly to methods of processing medical devices, such as self-expanding stents.

BACKGROUND

Aneurysms may occur in blood vessels at sites where the strength or resilience of the vessel wall is insufficient to prevent ballooning or stretching of the wall as blood passes through. If an aneurysm is left untreated, the blood vessel wall may expand and rupture, in some cases resulting in death.

Stent grafts may be used to treat aneurysms. A stent graft includes a graft material secured to a cylindrical scaffolding or framework of one or more stents. The stent graft may be introduced into a blood vessel percutaneously and deployed to span the aneurysmal sac. The stent(s) provide rigidity and structure to hold the graft material open in a tubular configuration as well as the outward radial force needed to create a seal between the graft material and a healthy portion of the vessel wall. Blood flowing through the vessel can be channeled through the hollow interior of the stent graft to reduce or eliminate the stress on the vessel wall at the location of the aneurysmal sac.

The stent(s) that make up the framework of the stent graft typically have a radially expandable geometry that allows the stent to be collapsed into a low profile configuration for delivery and then expanded at the treatment site to contact the vessel wall. Balloon-expandable stents expand in response to the inflation of a balloon, whereas self-expanding stents may deploy automatically when released from a delivery device.

Self-expanding stents are often fabricated from superelastic or shape memory alloys that can "remember" and recover a previous shape. In the case of nickel-titanium shape memory alloys, the source of the shape recovery is a phase transformation between a lower temperature phase (martensite) and a higher temperature phase (austenite) that may be driven by an increase in temperature (shape memory effect) or by the removal of an applied stress (superelastic effect).

The process of training a stent comprising a nickel-titanium alloy (which may also be referred to as "Nitinol" or "a Nitinol alloy") to have a particular remembered shape generally includes heat setting the stent while it is constrained in the configuration of interest. For example, a laser-cut Nitinol stent may be expanded and disposed about a mandrel having an outer diameter corresponding to the desired inner diameter of the expanded stent, and then heated at a temperature appropriate to "set" the desired expanded shape. In the case of wire stents comprising Nitinol, the wire may be formed into the desired expanded geometry for heat setting by a time-consuming process of bending the wire around pins projecting from a mandrel. Special care must be taken to avoid excessive bending of the Nitinol wire during the forming process, which can lead to fracture, and to restrain the wire during the positioning and heat setting in order to maintain the desired geometry about the mandrel.

BRIEF SUMMARY

An improved method of making a self-expanding stent from a nickel-titanium alloy wire is described in this disclosure. Also set forth is a method of forming a bend of a predetermined bend angle in a shape memory alloy wire. The wire including the bend may be used to form a self-expanding stent or another medical device, such as a wire guide, vena cava filter, or a fenestration or branch ring.

The method of making a self-expanding stent entails applying a bend stress sufficient to over-bend a portion of a wire by an amount in a range from about 85% to about 105%, where the wire comprises a nickel-titanium alloy and includes from about 40% to about 46% cold work. The bend stress is then released, thereby forming a bend having a predetermined bend angle in the wire. The application and release of the bend stress are repeated on successive portions of the wire in order to create a series of bends along a length of the wire in a predetermined bend pattern. The wire comprising the predetermined bend pattern is then positioned about a mandrel in an expanded stent geometry and heat set. Thus, a self-expanding stent is formed.

The method of forming a bend in a shape memory alloy wire entails applying a bend stress sufficient to over-bend a portion of a wire by an amount ranging from about 85% to about 105%, where the wire comprises a nickel-titanium alloy and includes from about 40% to about 46% cold work. The bend stress is then released to form a bend having a predetermined bend angle in the wire. The wire may be used for a guide wire, a self-expanding stent or another medical device.

DETAILED DESCRIPTION

A rapid and cost-effective method to fabricate self-expanding stents and other medical devices from shape memory alloy wire has been developed. When employed for stent fabrication, new method offers an alternative to the laborious process of winding Nitinol wire around pins projecting from a cylindrical mandrel to form an expanded stent geometry while ensuring that the wire is restrained in place. In the improved process, the nickel-titanium alloy wire includes a prescribed amount of cold work and is over-bent by a predetermined amount to form one or more bends in the wire that can be maintained without restraining the wire. Because the bends are formed before applying the wire to the mandrel, the wire can be positioned on the mandrel without wrapping around pins or applying tension to the ends. In addition, multiple stents can be formed on a single mandrel, further improving the efficiency of stent fabrication. The resulting self-expanding stents may be employed in variety of endovascular applications, including treatment of aneurysms.

Figure 1:
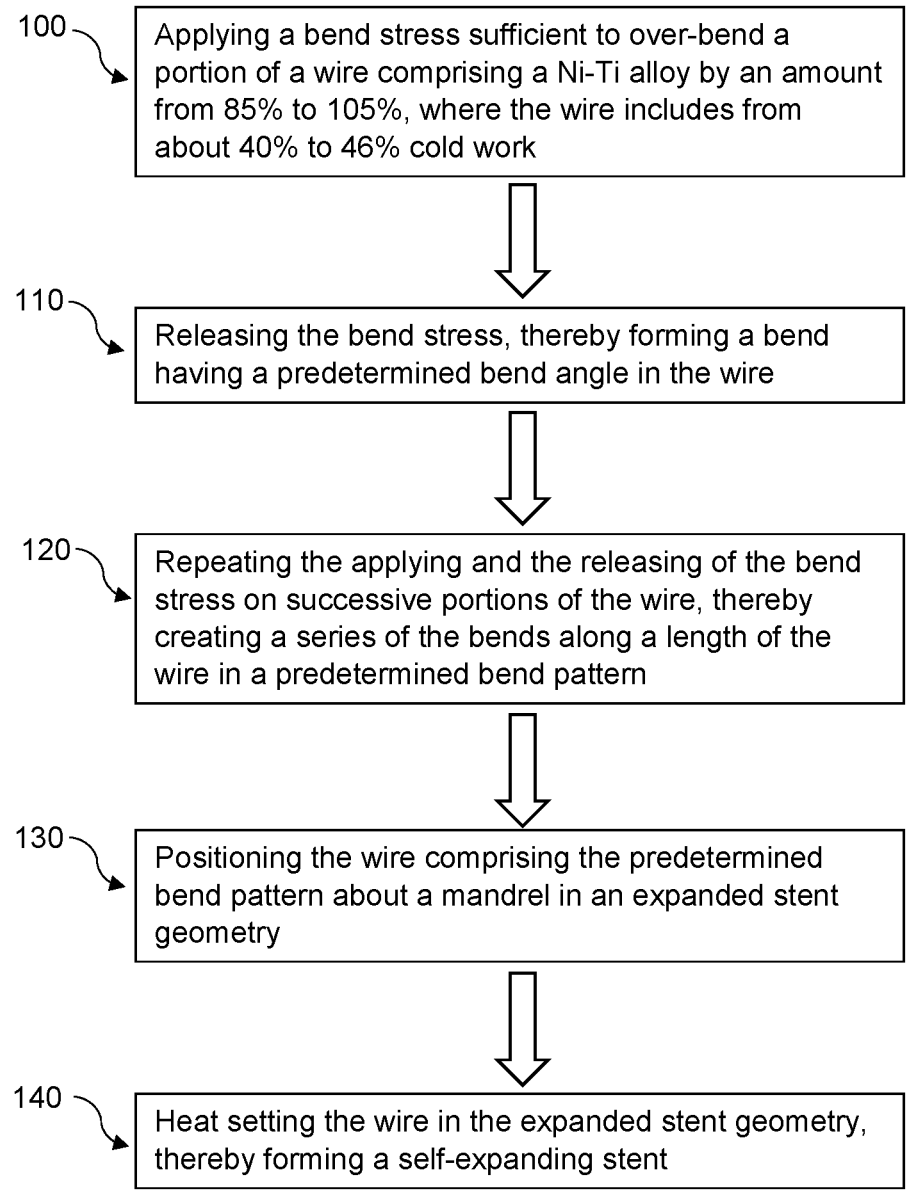
FIG. 1 is a flow chart showing steps of the method according to one embodiment.

Referring now to FIG. 1, the new method of fabricating a self-expanding stent includes applying 100 a bend stress sufficient to over-bend a portion of a wire comprising a nickel-titanium (Ni—Ti) alloy by an amount from about 85% to about 105%, where the wire includes from about 40% to about 46% cold work (and thus may be referred to as a cold-worked wire). Surprisingly, upon release 110 of the bend stress, the portion of the wire recoils to a bend having a desired bend angle. The application and release of the bend stress may be repeated 120 on successive portions of the cold-worked wire in order to create a series of bends along a length of the wire in a predetermined bend pattern. Typical as-drawn Nitinol wire that does not include from 40-46% cold work cannot retain a bent configuration without restraint, regardless of the amount of over-bending. In addition, typical as-drawn Nitinol wire may not have sufficient elasticity to avoid fracture during over-bending. In contrast, the cold-worked (40-46%) nickel-titanium alloy wire can achieve and retain a desired bend pattern when subjected to over-bending within the range of 85-105%. Below this over-bending range, the cold-worked wire may not return to the desired bend angle when the bending stress is released, and above this over-bending range, the cold-worked wire may fracture during bending.

A wire that has been "over-bent" has been bent beyond the desired bend angle by an amount that may be described in terms of a percentage, as determined from the following formula: 100·(OA−DA)/DA, where OA represents the over-bend angle and DA represents the desired bend angle with respect to a starting position of the wire. For example, to attain a 90° bend in a portion of the cold-worked wire, the portion may be over-bent to an angle of 180°, which corresponds to an over-bending amount equivalent to 100·(180°−90°)/90° or 100%. The over-bending may be carried out by bending the cold-worked wire over a mandrel having a radius larger than that of the cold-worked wire. Preferably, the radius of the mandrel is at least about two times larger than the radius of the cold-worked wire. It is believed that a maximum amount of strain that may be imparted to the outer surface of the cold worked wire during over-bending is about 30%.

The term "cold work" refers to plastic deformation imparted to a metal-based wire or other component without applying heat, and percent (%) cold work provides a measurement of the amount of the plastic deformation, where the amount is calculated as a percent reduction in a given dimension. For example, in wire drawing, the percent cold work may correspond to the percent reduction in the cross-sectional area of the wire resulting from one or more drawing passes through a die. Thus, a wire with 40-46% cold work may be understood to have been reduced in cross-sectional sectional area by 40-46% during cold drawing.

The nickel-titanium alloy of the wire is advantageously an equiatomic or near-equiatomic nickel-titanium alloy that exhibits superelastic behavior at body temperature, typically after heat setting at a suitable temperature. Such alloys may include an atomic ratio of nickel to titanium (at. % Ni:at. % Ti) in the range of from 45:55 to 55:45, where an equiatomic ratio is defined as 50:50 (50 at. % Ni:50 at. % Ti). The superelastic nickel-titanium alloy undergoes a reversible phase transformation between a martensitic phase and an austenitic phase that allows it to "remember" and return to a previous shape or configuration. Typically, recoverable strains of about 8-10% may be obtained from superelastic nickel-titanium alloys. The forward and reverse phase transformations may be driven by a change in stress (superelastic effect) and/or temperature (shape memory effect).

Slightly nickel-rich Nitinol alloys including, for example, about 51 at. % Ni and about 49 at. % Ti are known to be useful for medical devices which are superelastic at body temperature. In particular, alloys including 50.6-50.8 at. % Ni and 49.2-49.4 at. % Ti are considered to be medical grade Nitinol alloys and are suitable for use in the cold-worked wire. The nickel-titanium alloy may further include one or more additional alloying elements as substitutional elements for the nickel and/or titanium.

Referring again to FIG. 1, once the predetermined bend pattern is formed in the cold-worked wire by over-bending as described above, the wire may be positioned 130 about a mandrel (e.g., in a circumferential or helical configuration) to form an expanded stent geometry, and the wire may undergo 140 a heat setting treatment. As explained above, due to the capability of the cold-worked wire to retain the predetermined bend pattern without restraint, the wire may be positioned about the mandrel without winding around pins or applying any substantial tension to ends of the wire. (The term "substantial tension" may generally be understood to mean an applied tensile force in excess of about 2 lb, although the value may depend on the wire diameter/width.) Once the wire is in place on the mandrel, the wire may be heat set at a suitable temperature, thereby imparting a "memory" of the expanded stent geometry that includes the predetermined bend pattern. Thus, a self-expanding stent may be formed.

Heat setting is typically carried out at a temperature between about 300° C. and about 550° C. for a time duration from about 5 min to about 60 min. A fluidized bed may be employed for heat setting to ensure uniformity of the heating. As known to those of skill in the art, heat-setting of nickel-titanium alloys is carried out to impart a "memory" of a desired shape and to adjust the transformation temperatures. For example, if the cold-worked wire constitutes part or all of a medical device, such as a stent, which is to be deployed superelastically in a body vessel from a delivery configuration, then it is desirable for nickel-titanium alloy to "remember" a deployed (e.g., expanded) configuration. It is also advantageous for the component to be fully austenitic at body temperature, with austenite transformation temperatures ($A_s$ and $A_f$) lower than body temperature (i.e., less than 37° C.) and preferably lower than room temperature (e.g., about 20° C.-25° C. or less), so that the medical device deploys automatically when released from a delivery device. For example, a suitable value of $A_f$ may be between −15° C. and 25° C.

The series of bends may be formed in the cold-worked wire manually or automatically (e.g., using a programmable wire bending apparatus). For example, suitable wire bending machines are commercially available from Wafios Machinery Corporation (Branford, Conn.). As discussed above, each bend may be formed by over-bending a portion of the wire by an amount ranging from about 85% to about 105%; when the bending force is released, the portion of the wire may recoil from the over-bend angle to the desired bend angle. Using a programmable wire bending machine, an over-bending amount within the above-mentioned range may be automatically applied to successive portions of the wire in order to form the series of bends in the predetermined bend pattern, which may be a zigzag pattern of alternating hills and valleys, or another two- or three-dimensional bend pattern. An exemplary zigzag bend pattern may be found, for example, in the structure of Zenith® stents made by Cook Medical Technologies LLC (Bloomington, Ind.). Stents having a helical zigzag bend pattern are described, for example, in U.S. Patent Application Publication 2010/0198333, which is hereby incorporated by reference in its entirety. Each bend may have an included angle in a range from about 10° to about 150°, or from about 10° to about 80°. The bends in a predetermined bend pattern may be substantially identical or they may be different from each other (in terms of bend angle, size of the portion that undergoes bending, or other characteristics).

The cold-worked wire may have a diameter or width in a range from about 0.01 mm to about 10 mm, and more typically from about 0.1 mm to about 2 mm. The cold-worked wire may be solid or hollow, and may be a round wire or a flat wire with a circular, oval, square, rectangular or other cross-section. For some applications, the cold-worked wire may have a core-shell structure with a shell radially surrounding an elongated core. The core and shell may be formed from two different materials by coextrusion, vapor deposition, or another method. In one example, a radiopaque metal with high x-ray visibility, such as platinum or gold, may form the core and the nickel-titanium alloy may form the shell of the core-shell structure.

A number of approaches may be suitable for positioning the cold-worked wire about the mandrel to form the expanded stent geometry. For example, the cold-worked wire may be formed into a ring having an inner diameter comparable to, but preferably slightly larger than, an outer diameter of the mandrel. The ring may be slid over the mandrel such that the predetermined bend pattern extends circumferentially around the mandrel. The ends of the cold-worked wire may be secured together by a sleeve or other connector, typically prior to sliding the ring over the mandrel. Another approach to positioning the wire about the mandrel to form the expanded stent geometry may entail wrapping the cold-worked wire around the mandrel and then securing the ends of the wire. The ends of the wire may be secured together or each end may be individually secured to the mandrel (e.g., when the cold-worked wire is formed into a helical configuration). As would be recognized by one of ordinary skill in the art, the mandrel does not require radially projecting pins. Depending on the length of the mandrel, a number of cold-worked wires, each comprising the same or different predetermined bend patterns, may be positioned circumferentially about the mandrel prior to heat setting.

Typically, the mandrel has a circular transverse cross-section with an outer diameter in a range from about 4 mm to about 46 mm, or even larger. Accordingly, the self-expanding stent may have an expanded diameter from about 4 mm to about 46 mm, or larger. After fabrication of the self-expanding stent, a graft material may be attached thereto to define a tubular lumen for fluid flow, thereby forming a stent graft. Any of a number of known graft materials, such as biocompatible polymers, may be employed. The graft material may be attached to the self-expanding stent using methods known in the art, such as by stitching using a monofilament or braided suture material. An entirety or only a portion of the stent may be covered by the graft material, which may overlie or underlie the stent.

Figure 2:
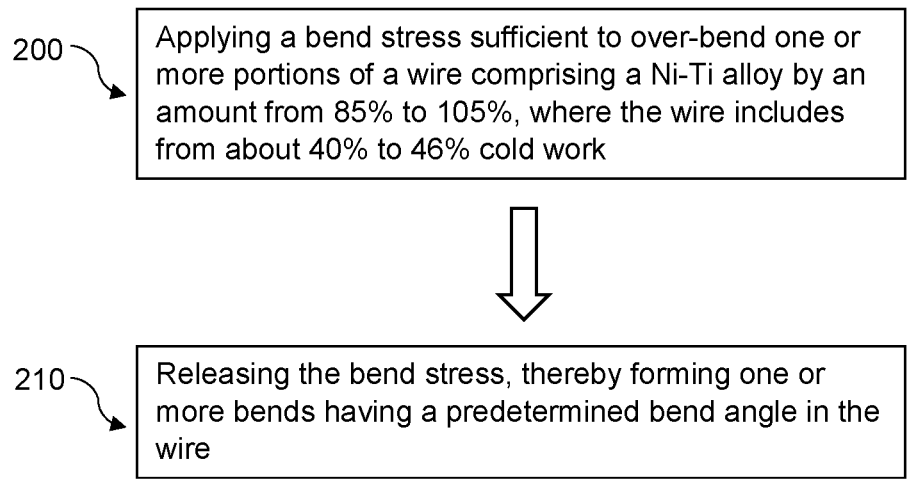
FIG. 2 is a flow chart showing steps of the method according another embodiment.

While the above-described over-bending process is particularly advantageous for fabricating self-expanding stents from nickel-titanium alloy wire, the process is not limited to stent fabrication. For example, the method may be used to form a bend in a shape memory alloy wire that may be employed as a wire guide or used in another medical device, such as a vena cava filter, or a fenestration or branch ring. Referring to FIG. 2, the method may entail applying 200 a bend stress sufficient to over-bend a portion of a wire comprising a nickel-titanium alloy by an amount ranging from 85% to 105%, where the wire includes from about 40% to 46% cold work, and then releasing 210 the bend stress, thereby forming a bend having a predetermined bend angle in the wire. The process may be repeated to form a series of bends in the wire. The additional steps of positioning the wire about a mandrel and/or heat setting the wire, as described in detail above, may not be required, depending on the requirements of the medical device.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of making a self-expanding stent, the method comprising:

applying a bend stress sufficient to over-bend a portion of a wire comprising a nickel-titanium alloy by an amount in a range from 85% to 105%, where the wire includes from about 40% to 46% cold work, and wherein a maximum amount of strain imparted to an outer surface of the wire during over-bending is about 30%;

releasing the bend stress, thereby forming a bend having a predetermined bend angle in the wire;

repeating the applying and releasing of the bend stress on successive portions of the wire, thereby creating a series of the bends along a length of the wire in a predetermined bend pattern, where the predetermined bend pattern is a zigzag pattern;

positioning the wire comprising the predetermined bend pattern about a mandrel in an expanded stent geometry, the positioning comprising forming the wire into a ring; securing ends of the wire together; and sliding the ring over the mandrel; and after the positioning, heat setting the wire in the expanded stent geometry, thereby forming a self-expanding stent.

2. The method of claim 1, wherein the positioning is carried out without applying any substantial tension to ends of the wire.

3. The method of claim 1, wherein a plurality of the wires, each comprising the predetermined bend pattern, are positioned about the mandrel prior to heat setting.

4. The method of claim 1, wherein the wire is not restrained on the mandrel during the heat setting.

5. The method of claim 1, wherein the heat setting is carried out at a temperature in a range from about 300° C. to about 550° C.

6. The method of claim 5, wherein the heat setting takes place in a fluidized bed.

7. The method of claim 1, wherein the applying and the releasing of the bend stress is carried out automatically using a programmable wire bending apparatus.

8. The method of claim 1, wherein each of the bends in the predetermined bend pattern comprises an included angle in a range from about 10° to about 150°.

9. The method of claim 1, wherein the mandrel does not include radially projecting pins.

10. The method of claim 1, wherein the mandrel has a circular transverse cross-section with a diameter in a range from about 4 mm to about 46 mm.

11. The method of claim 1, wherein the wire comprises a near-equiatom nickel-titanium alloy comprising an atomic ratio of nickel to titanium in a range from 45:55 to 55:45.

12. The method of claim 1, wherein the wire has a core-shell structure with a shell radially surrounding an elongated core, and wherein the core or the shell comprises the nickel-titanium alloy.

13. The method of claim 1, further comprising, after forming the self-expanding stent, attaching a graft material thereto, thereby forming a stent graft.

14. A method of forming a bend of a predetermined bend angle in a shape memory alloy wire, the method comprising:
 applying a bend stress sufficient to over-bend a portion of a wire comprising a nickel-titanium alloy by an amount ranging from 85% to 105%, where the wire includes from about 40% to 46% cold work, and wherein a maximum amount of nonrecoverable strain imparted to an outer surface of the wire during over-bending is about 30%; and
 releasing the bend stress, thereby forming a bend having a predetermined bend angle in the wire;
 repeating the applying and releasing of the bend stress on successive portions of the wire, thereby creating a series of the bends along a length of the wire in a predetermined bend pattern, where the predetermined bend pattern is a zigzag pattern;
 positioning the wire comprising the predetermined bend pattern about a mandrel in an expanded stent geometry, wherein the positioning is carried out without applying tension to ends of the wire; and
 after the positioning, heat setting the wire in the expanded stent geometry, thereby forming a self-expanding stent.

* * * * *